(12) United States Patent
Jang et al.

(10) Patent No.: US 6,924,652 B2
(45) Date of Patent: Aug. 2, 2005

(54) METHOD FOR DETERMINING OPTIMAL DEGREE OF VULCANIZATION AND OPTIMAL CONTENT OF CONSTITUENT INGREDIENT OF COMPOSITION FOR VULCANIZATION IN REAL TIME BY IMPEDANCE MEASUREMENT AND ANALYSIS

(75) Inventors: Jee-Hwan Jang, Daejeon (KR); Hyun-Kyung Sung, Daejeon (KR); Hun-Jong Baik, Daejeon (KR); Ho-Sull Lee, Daejeon (KR)

(73) Assignee: Korea Kumho Petrochemical Co., Ltd. (KR)

( * ) Notice: Subject to any disclaimer, the term of this patent is extended or adjusted under 35 U.S.C. 154(b) by 0 days.

(21) Appl. No.: 10/322,903

(22) Filed: Dec. 18, 2002

(65) Prior Publication Data

US 2003/0134987 A1 Jul. 17, 2003

(30) Foreign Application Priority Data

Jan. 9, 2002 (KR) ......................................... 2002-1152

(51) Int. Cl.$^7$ .............................................. G01R 27/26
(52) U.S. Cl. ...................... 324/663; 324/607; 324/658
(58) Field of Search ................................ 324/663, 607, 324/658

(56) References Cited

U.S. PATENT DOCUMENTS 4,868,769 A * 9/1989 Persson ....................... 702/30
6,502,046 B1 12/2002 Yoon et al.

FOREIGN PATENT DOCUMENTS

KR           10-257965           3/2000

OTHER PUBLICATIONS

Magil, R. et al, 'Process Machinery—Using Real–Time Impedance Measurement to Monitor and Control Rubber Vulcanization,' Rubber World, pp. 24–28, & 62, Dec., 1999.
Nah, C. et al, 'Effects of Vulcanization Type and Temperature on Physical Properties of Natural Rubber Compounds,' Elastomer, vol. 35, No. 3, pp. 173–179, 2000.
Park, B.H. et al, 'Effect of Various Cross–Linking Types on the Physical Properties in Carbon Black–Filled Natural Rubber Compound,' Polymer (Korea), vol. 25, No. 1, pp. 63–70, 2001.
J. Macdonald, "Impedance Spectroscopy" Emphasizing Solid Materials and Systems a Wiley Interscience Publication, (1987).

* cited by examiner

Primary Examiner—Robert D. Harlan
(74) Attorney, Agent, or Firm—Cook, Alex, McFarron, Manzo, Cummings & Mehler, Ltd.

(57) ABSTRACT

The present invention relates to a method for evaluating the crosslink degree of a vulcanized sample in real time during a vulcanization process or diagnosing the electrical properties of the sample after the completion of the vulcanization process, and then determining an optimal vulcanization time and an optimal content of each constituent gradient of a composition for vulcanization that optimize the properties of the composition according to the vulcanization conditions, for the sake of improving the properties of the vulcanized sample prepared from a polymer by vulcanization at a high temperature.

The method for determining an optimal vulcanization time and an optimal content of each constituent gradient of a composition for vulcanization that optimize the properties of the composition according to the vulcanization conditions includes: (a) measuring an impedance spectrum in a specific frequency range in the individual vulcanization condition; (b) approximating the measured impedance spectrum to an equivalent circuit model consisting of resistance and capacitance components; (c) determining a polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) from the determined parameters; (d) determining, as an optimal end point of vulcanization, a time point at which the increasing rate of the polymer resistance Rp rapidly slows down; and (e) determining the optimal content of each constituent ingredient of the composition for vulcanization when the polymer resistance Rp of the sample completely vulcanized is at its minimum.

16 Claims, 2 Drawing Sheets

METHOD FOR DETERMINING OPTIMAL DEGREE OF VULCANIZATION AND OPTIMAL CONTENT OF CONSTITUENT INGREDIENT OF COMPOSITION FOR VULCANIZATION IN REAL TIME BY IMPEDANCE MEASUREMENT AND ANALYSIS

BACKGROUND OF THE INVENTION

1. The Field of the Invention

This invention relates to a method for evaluating the crosslink degree of a vulcanized sample in real time during a vulcanization process or diagnosing the electrical properties of the sample after the completion of the vulcanization process, and then determining an optimal vulcanization time and an optimal content of each constituent gradient of a composition for vulcanization that optimize the properties of the composition according to the vulcanization conditions, thereby improving the properties of the vulcanized sample prepared from a polymer by vulcanization at a high temperature.

2. Related Prior Art

The polymer vulcanization process takes a most time in the manufacture of polymer products in the rubber industry relating to general polymer materials such as tires. Thus steady and persistent efforts have been made to increase the vulcanization rate so as to shorten the required time of the vulcanization process. The conventional methods for reducing the required vulcanization time involve changing the vulcanization system to increase the vulcanization rate or raising the vulcanization temperature. For the method of changing the vulcanization system, a novel crosslink agent of a high vulcanization rate is an essential prerequisite. On the other hand, the method of increasing the vulcanization temperature is effective in reducing the required vulcanization time but changes the crosslinking structure or the crosslink degree depending on the thermal stability of the used polymer or vulcanization system, thus deteriorating the mechanical properties of the polymer composition. For that reason, polymer type, vulcanization system and required properties are the points to be specially considered in reducing the required vulcanization time by raising the vulcanization temperature (See. Elastomer, Vol. 35, No. 3, pp 173–179 (2000)).

The vulcanization reaction is a typical method of forming a three-dimensional reticular structure through a crosslink between main chains of a polymer composition, for example, natural rubber (NR), isoprene rubber (IR), butadiene rubber (BR), styrene butadiene rubber (SBR), butyl rubber (IIR), ethylene propylene rubber (EPDM), chloroprene rubber (CR), chlorosulfonated polyethylene (CSP), nitrile rubber (NBR), acryl rubber, urethane rubber, silicon rubber, fluorine rubber, etc. to enhance the required properties of the polymer composition such as restoring force, elastic properties and the like. There are different types of crosslink formed in the vulcanization reaction. The crosslink widely used in the tire industry is formed by vulcanization introducing polysulfide (—C—Sx-C—, where x is 1 to 4), or by carbon-carbon (C—C) bonding and resinous crosslinking between the main chains of the polymer to increase thermal stability and ageing properties. Recently, the hybrid crosslink that enhances the thermal stability of the polymer is widely used to prevent a deterioration of the properties caused by overcure in the case of crosslinking at a high temperature. The properties of the polymer composition obtained by the vulcanization reaction are greatly dependent on the crosslink density as well as the crosslink type. For instance, the vulcanized crosslinking provides high tensile strength and low thermal ageing characteristic. On the contrary, the carbon-carbon bonding provides high thermal ageing characteristic, low tensile strength and low fatigue fracture. The individual properties appear differently even in a single vulcanization reaction in such a manner that the crosslink density and the modulus of a sample are increased with the progress of vulcanization, but the tensile strength is increased and then decreased with an increase in the crosslink density (See. Polymer (Korea), Vol. 25, No. 1, pp 63–70 (2001)). The vulcanization reaction is a process of adding sulfur or another crosslink agent to the polymer to form a strong and firm crosslink between polymer molecules by pressurizing, heating or other means and to influence the properties of the product, thereby reducing deformation, increasing elastic and tensile strengths and decreasing swelling caused by the solvent used. To enhance the quality and performance of the polymer product with high productivity and reduce the production cost, it is necessary to use a method for effectively increasing the vulcanization rate, a method for preparing an optimal composition for vulcanization, and a method for analyzing the vulcanization process in real time to determine the end point of the vulcanization reaction.

Conventionally, a rheometer method and an impedance measurement method using the scanning of a single frequency have been used to measure the crosslink degree and the crosslink rate of a sample in real time during the vulcanization process in order to improve the properties of the sample prepared from a polymer by vulcanization at high temperature. The rheometer is also called "an oscillating disc rheometer", which has a rotor causing sinusoidal vibrations three times every minute to deform the rubber and describes a rheometer curve plotting the torque at the rotor axis versus time. The vulcanization rate is measured from the rheometer curve. To calculate the vulcanization rate, a line passing the minimum and maximum values of the torque marked on the curve and parallel with the time axis is first drawn. A second line is drawn to pass the points respectively amounting to 30% and 90% of the line distance and be parallel with the time axis. Then the crosslink time until the second line intersects the vulcanization curve is referred to as t30 and t90, respectively. Subtracting t30 from t90 gives the vulcanization rate. A low value of the calculation means a high vulcanization rate and, in this case, the required vulcanization time of the polymer product is short (See. KP 257,965). In the rheometer method, however, it is necessary to use very expensive rheometer equipment and to keep clean the surface of the oscillating disc being in contact with the vulcanized composition in every vulcanization reactor and the surface of the inner wall of the reactor for the sake of precisely measuring the torque variations of the sample over time. When the shelf time after mixing the composition for vulcanization used for the vulcanization process and all the temperature variations of samples controlled in the vulcanization process are not constant, a considerable error on the vulcanization rate may occur in the rheometer method that measures the macroscopic properties of the sample. It is therefore necessary to establish criteria for evaluation of the vulcanization rate based on the concept of standard deviation. This requires a little over-vulcanization in determining the end point of the vulcanization process, thus increasing the required vulcanization time, and the over-vulcanization inevitably causes a slight deterioration of the properties in the part of the sample. On the other hand, the method for determining the end point of vulcanization by impedance measurement and analysis of the vulcanized sample in real time through the scanning of a single frequency is disclosed by Richard Magill at Signature Control Systems Co. (See. Rubber World, Vol. 221, No. 3, pp 24–28, 62, (1999)). According to this method, the response of the vulcanized sample to a specific frequency (for example, 9 kHz) appears as complex impedance that consists of in-phase (conductance) and out-of-phase (capacitance) components. The conductance component results from the fast movement of ions in the sample and conductance, and the capacitance component is a measure of determining how fast the dipoles in the sample orient to the externally applied single frequency. The orientation speed of dipoles to the frequency applied is generally limited because the hardness of the polymer increases with the progress of the vulcanization process. The reciprocal of the capacitance component measured in real time during the vulcanization process is in accord with the tendency of torque variations observed in the known rheometer method. Thus the measurement of the capacitance component enables the evaluation of the degree of vulcanization and the vulcanization rate. However, the evaluation method using a single high frequency (e.g., 9 kHz) in consideration of fast dynamics in the sample during the vulcanization process is unsatisfactory in accurately predicting all the internal characteristics and properties (including slow dynamics) of the vulcanized sample. The sample during the vulcanization process contains considerably numerous types of ions and dipoles and the internal ion and dipole components are changing at any time with an elapsed time of vulcanization. The mobility of several ions generally shows the slow dynamic characteristic and appears in response to the low frequency. Especially, the behavior of bulky ions can be observed only in the lower frequency range, and the sample evaluation method using the scanning of a single frequency hardly reflects the low dynamics of the sample. Accordingly, the whole wide frequency range (10 kHz to 1 Hz) must be taken into consideration as will be described in the present invention for the sake of the complete analysis and evaluation of a sample in the level of molecule.

As a most basic test in evaluating the properties of a vulcanized sample, the testing method specified in KS M 6518 is applied. First, a thin sample sheet is cut into four dumbbell-shaped test pieces, of which the thickness is then measured with a thickness gauge. Once making 20-mm and 40-mm marks, the test pieces are measured in regard to length and cutting load the moment that they are cut by a tensile tester. The tensile strength and the elongation percentage are calculated according to predefined equations. But the tensile test requires a number of samples and takes a long time for measurement (See. KP 257,965). Besides, the methods for measuring the properties of a vulcanized sample may include exothermic test, tearing energy measurement, repulsive elasticity test, durability test, BFG cutting and chipping characteristic test, all of which still require a long time for measurement of the properties (See. Polymer (Korea), Vol. 25, No. 1, pp 63–70 (2001)).

SUMMARY OF THE INVENTION

It is therefore an object of the present invention to solve the problems with the prior art and to provide an optimal method for controlling vulcanization in real time through impedance measurement and analysis of a polymer, thereby accurately evaluating the internal properties of the vulcanized polymer sample over time in the vulcanization process.

It is another object of the present invention to provide a method for diagnosing the electrical characteristics of a sample completely vulcanized and thereby determining the optimal content of each constituent ingredient of a composition for vulcanization with optimized properties according to the vulcanization conditions.

To achieve the above objects of the present invention, there is provided a method for evaluating the crosslink degree of a vulcanized sample in real time during a vulcanization process or diagnosing the electrical properties of the sample after the completion of the vulcanization process, and then determining an optimal vulcanization time and an optimal content of each constituent gradient of a composition for vulcanization that optimize the properties of the composition according to the vulcanization conditions, thereby improving the properties of the vulcanized sample prepared from a polymer by vulcanization at a high temperature. In the present invention, the whole frequency range (10 kHz to 1 Hz) of the measured impedance spectrum is taken into consideration in the analysis process. Also, the present invention approximates the impedance spectrum to a physically adequate equivalent circuit model of a vulcanized sample and thereby determines the physical properties of the vulcanized sample as capacitance and resistance components representing the microscopic internal characteristics of the sample in the level of molecule. Especially, the resistance component can be obtained by approximation to the resistance of carbon black itself and the resistance component of the polymer material. The resistance component greatly depends on the constituent ingredients of the composition for vulcanization used in the vulcanization process, the crosslinking method used for vulcanization, the temperature, and the crosslink degree. These internal resistance characteristics of the vulcanized sample can be used alone or in combination as the final criteria for the properties of the vulcanized sample and, accordingly, suitably applied for the purpose of accurately evaluating the internal properties of the vulcanized sample over time or of the sample completely vulcanized.

The method for controlling a degree of vulcanization for a vulcanized sample in real time and determining an optimal content of each constituent ingredient of a composition for vulcanization includes: (a) measuring an impedance during a vulcanization process in real time so as to evaluate a crosslink degree of the vulcanized sample or the properties of the sample completely vulcanized; (b) approximating the measured impedance spectrum to an equivalent circuit model of the sample and determining parameters for resistance and capacitance components of the equivalent circuit model; (c) determining a polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) from the determined parameters; (d) determining, as an optimal end point of vulcanization, a time point at which the increasing rate of the polymer resistance Rp rapidly slows down; and (e) determining the optimal content of each constituent ingredient of the composition for vulcanization when the polymer resistance Rp of the sample completely vulcanized is at its minimum.

More specifically, the present invention includes fitting impedance data measured in the frequency range of 10 kHz to 1 Hz using an adequate analysis software according to a method disclosed in U.S. patent application Ser. No. 09/476,452; determining a polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) among various resistance parameters; determining, as an optimal end point of vulcanization, a time point at which the increasing rate of the polymer resistance Rp rapidly slows down; and determining the optimal content of each constituent ingredient of the composition for vulcanization when the polymer resistance Rp of the sample completely vulcanized is at its minimum. Compared with the conventional methods for evaluating vulcanization through torque variations and tensile test, the present invention is more efficient to optimize the properties of the vulcanized sample. The present invention is also a non-destructive testing method that takes a very short time of about one minute in the measurement and evaluation for securing excellent properties of the vulcanized sample and an accurate end point of vulcanization, relative to the conventional methods such as rheometer method or tensile testing method.

DETAILED DESCRIPTION OF THE INVENTION

Hereinafter, the preferred embodiments of the present invention will be described in detail with reference to the accompanying drawings by way of the following examples, which are not intended to limit the scope of the present invention.

EXAMPLES 1, 2 and 3

The samples used in measuring the variations of the properties of rubber during the crosslinking process were prepared with the compositions as listed in Table 1 according to a known method prior to the crosslinking process. The synthetic rubber as used in the test was styrene butadiene rubber (SBR) supplied from Korea Kumho Petrochemical Co., Ltd. The samples in Examples 1, 2 and 3 were different from one another in the content of sulfur and vulcanization accelerating agent in the rubber composition for vulcanization.

TABLE 1

| Example<br>Sample | 1<br>S1 | 2<br>S2 | 3<br>S3 |
|---|---|---|---|
| Synthetic rubber | 137.5 | 137.5 | 137.5 |
| Carbon black | 68.75 | 68.75 | 68.75 |
| Zinc oxide | 3.0 | 3.0 | 3.0 |
| Stearic acid | 1.0 | 1.0 | 1.0 |
| Sulfur | 1.0 | 2.0 | 3.0 |
| Vulcanization accelerating agent | 1.0 | 2.0 | 3.0 |

EXAMPLES 4, 5 and 6

The samples used in measuring the properties of the rubber after the completion of vulcanization were prepared with the compositions as listed in Table 2 according to a known method prior to the crosslinking process. Then, the vulcanization time was varied depending on the content of sulfur and vulcanization accelerating agent in the rubber composition for vulcanization. The vulcanization time based on the content was measured using a known rheometer method. The synthetic rubber as used in the test was SBR supplied from Korea Kumho Petrochemical Co., Ltd. The samples in Examples 4, 5 and 6 were different from one another in the content of sulfur and vulcanization accelerating agent in the rubber composition for vulcanization and the vulcanization time.

TABLE 2

| Example<br>Sample | 1<br>S1-1 | 2<br>S2-1 | 3<br>S3-1 |
|---|---|---|---|
| Synthetic rubber | 137.5 | 137.5 | 137.5 |
| Carbon black | 68.75 | 68.75 | 68.75 |
| Zinc oxide | 3.0 | 3.0 | 3.0 |
| Stearic acid | 1.0 | 1.0 | 1.0 |
| Sulfur | 1.0 | 2.0 | 3.0 |
| Vulcanization accelerating agent | 1.0 | 2.0 | 3.0 |
| Vulcanization temperature (° C.) | 145 | 145 | 145 |
| Vulcanization time (min) | 41 | 35 | 29 |

EXAMPLE 7

Now, a specific example of measuring the variations of the properties of the rubber during the crosslinking process will be described in detail. The following description will be given to the real-time property measurement for samples S1, S2 and S3 of Examples 1, 2 and 3, respectively, which are different from one another in the content of sulfur and vulcanization accelerating agent in the rubber composition for vulcanization.

Figure 3:
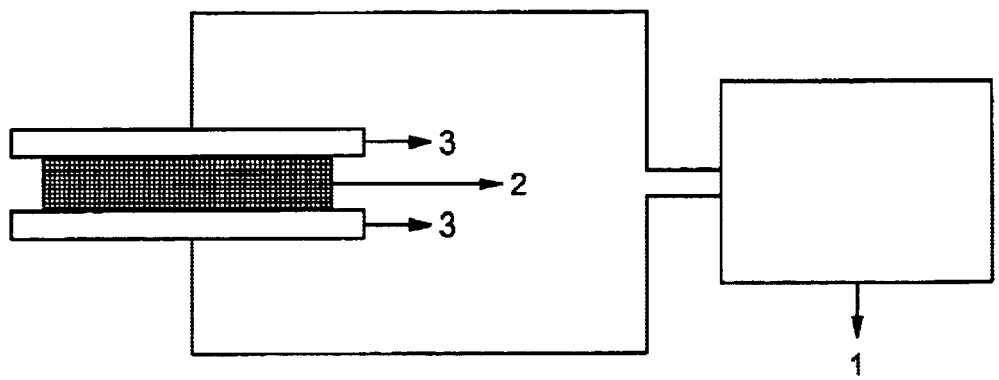
FIG. 3 is a diagram showing a model realizing the present invention using impedance measuring equipment with a sample positioned between two measurement electrodes.

(a) The measurement of impedance was performed to evaluate the crosslink degree of the vulcanized samples in real time during the vulcanization process. The impedance spectrum was measured in an adequate frequency range (10 kHz to 1 Hz) for determining the parameters of an equivalent circuit model used in the spectrum analysis. A battery diagnosis system (Powergraphy™, model name: BPS 1000FL) supplied from Korea Kumho Petrochemical Co., Ltd. was used in the impedance measurement. For the real-time impedance measurement during vulcanization at a high temperature (150° C.), as shown in FIG. 3, rubber samples S1, S2 and S3 were positioned between two flat electrodes 3 and measured in regard to impedance at a high speed with BPS 1000FL impedance measurement equipment 1. The two flat electrodes 3 were made from any one metal selected from aluminum, copper, nickel, platinum and stainless steel. In FIG. 3, reference numeral 1 denotes the impedance measurement equipment, reference numeral 2 the test samples, the reference numeral 3 the electrodes for impedance measurement.

Figure 4:
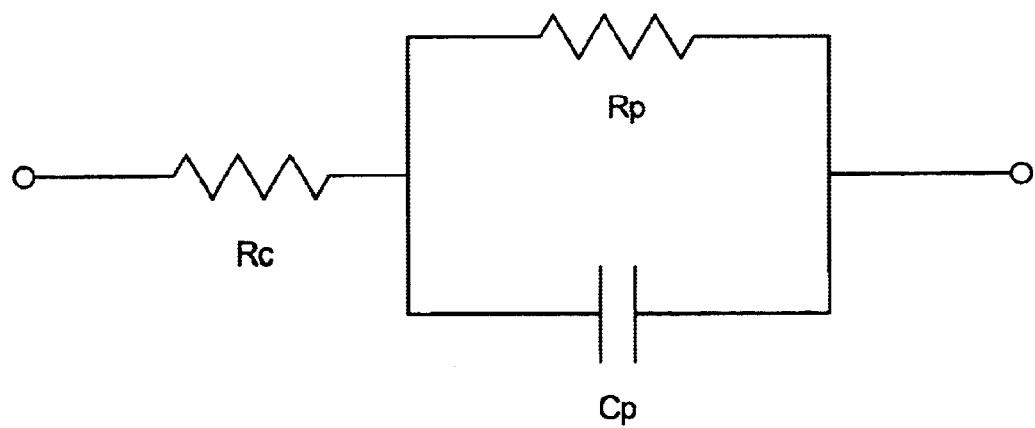
FIG. 4 is an example of the equivalent circuit model for vulcanized samples, where Rc is the resistance of carbon black, Rp the resistance of a polymer material, Cp the capacitance component of the polymer material.

(b) The measured impedance spectrum was approximated to an equivalent circuit model for vulcanized samples to determine the resistance and capacitance components of the equivalent circuit model. The impedance spectrum curves measured for the three rubber compositions for vulcanization in the step (a) were approximated to the equivalent circuit model shown in FIG. 4. The equivalent circuit model was selected for optimizing the approximation of the impedance spectrum. The equivalent circuit model as used in the present invention was a 1RC model that consists of three parameters physically related to the samples, including resistance components Rc and Rp and capacitance component Cp. These three parameters were determined by a fitting method approximating the above-mentioned impedance spectrum curves to the equivalent circuit model for vulcanized samples using the nonlinear least square method. In the present invention, the equivalent circuit model is not specifically limited to the 1RC model and any multi-order RC model represented by nRC (where n is a positive integer) is available.

Figure 1:
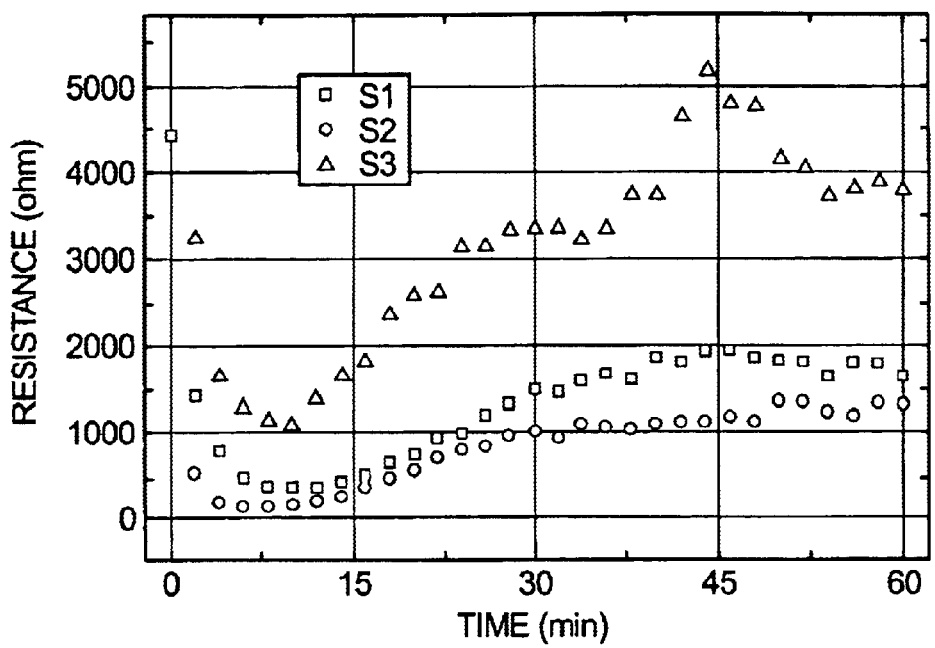
FIG. 1 is a graph plotting the real-time variation of resistance Rp of three composition samples for vulcanization having a different sulfur content versus an elapsed vulcanization time, after measuring and analyzing the impedance of the three composition in a wide frequency range (10 kHz to 1 Hz) during the real-time vulcanization process.

(c) From the approximated parameters, the variation of the polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) was measured with an elapsed vulcanization time. Among the three parameters obtained by fitting the impedance data to the 1RC equivalent circuit model in the step (b), the Rp value varying with an elapsed vulcanization time was determined for the three composition samples for vulcanization. The results of the variation of Rp value versus elapsed vulcanization time are presented in FIG. 1. Referring to FIG. 1, the Rp value of all the three samples decreases in the early stage and then gradually increases over time. At a certain time point, the increasing rate of the Rp value is rapidly dropped or the Rp value decreases again.

(d) Regarding the elapsed vulcanization time, the time point at which the increasing rate of the Rp value slows down is determined as an optimal end point of vulcanization. In FIG. 1, the Rp value decreases in the early stage of vulcanization presumably because a considerable part of the sulfur and the vulcanization accelerating agent included in the rubber composition for vulcanization are transformed into ions or radicals in the high-temperature vulcanization conditions, thereby increasing the ionic conductivity of the rubber polymer, or the ions or radicals generated attack the double bonds in the main chain of the rubber polymer to cause vulcanization to some extent, forming a chemical bond between carbon and sulfur atoms to provide a conductive reticular structure in the rubber composition. Subsequently, the Rp value rapidly increases with an elapsed vulcanization time, which is presumably because ions or radicals less produced at a high temperature attack the double bonds in the main chain of the rubber polymer to form chemical bonds between carbon and sulfur atoms. In such a vulcanization step, ions or radicals are used up and the hardness of the rubber composition rapidly increases, thereby extremely suppressing the movement of ions and the rearrangement of the radical and dipolar components. After this, the Rp value is nearly constant with an elapsed vulcanization time in a time interval where intermittent equilibrium occurs that the production rate of forming disulfide and polysulfide in the vulcanization step at a high temperature and ions or radicals resulting from the initial decomposition of sulfur is almost equal to the vulcanization rate of forming the chemical bonds between carbon and sulfur atoms by the ions or radicals attacking the double bonds in the main chain of the rubber polymer. In the equilibrium interval, the ion concentration and the crosslink density are almost constant, and the optimal end point of the vulcanization process appears. Then the Rp value decreases with an elapsed vulcanization time, which is presumably because disulfide or polysulfide generated from vulcanization at a high temperature are gradually decomposed into ions or radicals to cause over-vulcanization, forming a short crosslink structure such as monosulfide and disulfide in the vulcanized sample, thereby slowly reducing the hardness of the rubber composition.

EXAMPLE 8

Now, a specific example of measuring the properties of rubber samples after the completion of the vulcanization process will be described in detail. The following description will be given to the property measurement for samples S1-1, S2-1 and S3-1 of Examples 4, 5 and 6, respectively, which are different from one another in the required vulcanization time and the content of sulfur and vulcanization accelerating agent in the rubber composition for vulcanization.

(a) The measurement of impedance was performed to evaluate the properties of the samples completely vulcanized. The impedance spectrum was measured in an adequate frequency range (10 kHz to 1 Hz) for determining the parameters of an equivalent circuit model used in the spectrum analysis. A battery diagnosis system (Powergraphy™, model name: BPS 1000FL) supplied from Korea Kumho Petrochemical Co., Ltd. was used in the impedance measurement. For the real-time impedance measurement of the vulcanized samples, as shown in FIG. 3, rubber sample pieces S1-1, S2-1 and S3-1 were positioned between two flat electrodes and measured in regard to impedance at a high speed at the room temperature with BPS 1000FL impedance measurement equipment.

(b) The measured impedance spectrum was approximated to an equivalent circuit model for vulcanized samples to determine the resistance and capacitance components of the equivalent circuit model. The impedance spectrum curves measured for the three vulcanized samples in the step (a) were approximated to the equivalent circuit model shown in FIG. 4. The equivalent circuit model was selected for optimizing the approximation of the impedance spectrum. The equivalent circuit model as used in the present invention was a 1RC model that consists of three parameters physically related to the samples, including resistance components Rc and Rp and capacitance component Cp. These three parameters were determined by a fitting method approximating the above-mentioned impedance spectrum curves to the equivalent circuit model for vulcanized samples using the nonlinear least square method. In the present invention, the equivalent circuit model is not specifically limited to the 1RC model and any multi-order RC model represented by nRC (where n is a positive integer) is available.

Figure 2:
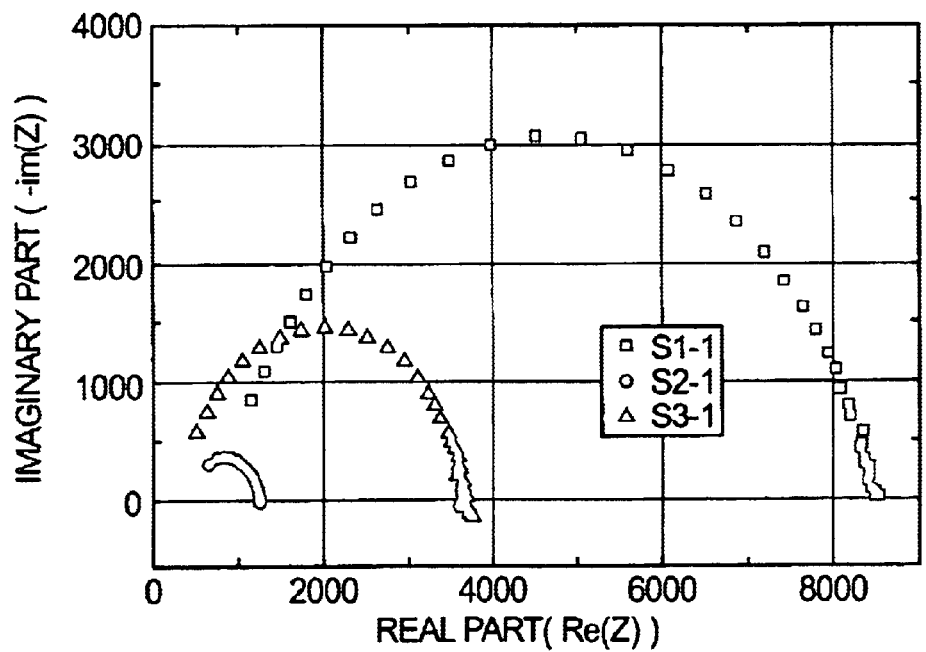
FIG. 2 is a graph showing a comparison of impedance spectrums measured in a wide frequency range (10 kHz to 1 Hz) for three composition samples of a different sulfur content after the completion of the vulcanization process.

(c) From the approximated parameters, the variation of the polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) was measured with an elapsed vulcanization time. Among the three parameters obtained by fitting the impedance data to the 1RC equivalent circuit model in the step (b), the Rp value varying depending on the content of sulfur and vulcanization accelerating agent in the rubber composition for vulcanization was determined for the three samples. The results of the impedance measurement are presented in FIG. 2. Referring to FIG. 2, the least magnitude of the semicircle in the Nyquist diagram, i.e., the Rp value is observed for the sample S2-1 in which the content of sulfur and vulcanization accelerating agent in the rubber composition is 2.0 phr.

(d) The optimal content of each constituent ingredient of the composition for vulcanization was determined at the smallest Rp value of the sample completely vulcanized. According to FIG. 2, the smallest Rp value is observed for the sample S2-1 in which the content of sulfur and vulcanization accelerating agent in the rubber composition is 2.0 phr. This is presumably because the vulcanization, by which ions or radicals generated during the vulcanization process attack the double bond in the main chain of the rubber polymer to form chemical bonds between carbon and sulfur atoms, occurs most vigorous when the content of sulfur and vulcanization accelerating agent in the rubber composition for vulcanization is greater than 2.0 phr (for example, 3.0 phr for S3-1), thereby rapidly increasing the hardness of the rubber composition and hence extremely suppressing the movement of ions and the rearrangement of radical and dipole components. When the content of sulfur and vulcanization accelerating agent in the rubber composition for vulcanization is less than 2.0 phr (for example, 1.0 phr for S1-1), a sharp increase in the hardness of the rubber composition by the vulcanization step hardly appear and a rise of the Rp value is suppressed to some degree. In this case, however, the phase separation between carbon black and rubber components occurs in the rubber composition and the vulcanization-induced effect of forming a conductive reticular structure in the rubber composition appears insignificantly. As a result, these effects are most optimally combined together and the Rp value is at its minimum when the content of sulfur and vulcanization accelerating agent in the rubber composition is 2.0 phr.

The above-mentioned rubber polymer material may include natural rubber (NR), isoprene rubber (IR), butadiene rubber (BR), styrene butadiene rubber (SBR), butyl rubber (IIR), ethylene propylene rubber (EPDM), chloroprene rubber (CR), chlorosulfonated polyethylene (CSP), nitrile rubber (NBR), acryl rubber, urethane rubber, silicon rubber and fluorine rubber.

As described above, the present invention includes fitting impedance data of a vulcanized sample measured in a frequency range of 10 kHz to 1 Hz using an adequate analysis software; determining a polymer resistance Rp (i.e., a value obtained by subtracting a real part of the impedance measurement at a maximum frequency from a real part of the impedance measurement at a minimum frequency, or the magnitude of a real part of the semicircle in a Nyquist diagram) among the above-obtained resistance parameters; determining, as an optimal end point of vulcanization, a time point at which the increasing rate of the polymer resistance Rp rapidly slows down; and determining the optimal content of each constituent ingredient of the composition for vulcanization when the polymer resistance Rp of the sample completely vulcanized is at its minimum. Compared with the conventional methods for evaluating vulcanization through torque variations and tensile test, the present invention is more efficient to optimize the properties of the vulcanized sample.

The present invention takes a very short time of about one minute in the measurement and evaluation process for securing excellent properties of the vulcanized sample and determining an accurate end point of vulcanization, relative to the conventional methods such as rheometer method or tensile testing method, thus reducing the required time for measurement and evaluation, and provides a vulcanized sample of excellent properties and optimal conditions for vulcanization to every company and institute related to the manufacture and research of the vulcanized sample of various polymer materials.

What is claimed is:

1. A method for controlling an optimal degree of vulcanization for a vulcanized sample in real time and determining an optimal content of each constituent ingredient of a polymer composition for vulcanization, the method comprising:
   (a) measuring an impedance during an actual vulcanization process in a frequency range of 1 Hz to 10 kHz so as to evaluate the properties of the vulcanized sample;
   (b) analyzing the measured impedance data for fitting to determine various parameters;
   (c) determining a polymer resistance Rp, among the parameters, with respect to an elapsed time of the vulcanization process;
   (d) determining, as an optimal end point of vulcanization, a time point at which the increasing rate of the polymer resistance Rp rapidly slows down; and
   (e) determining the optimal content of each constituent ingredient of the composition for vulcanization when the polymer resistance Rp of the sample completely vulcanized is at its minimum.

2. The method as claimed in claim 1, wherein the polymer resistance is obtained by subtracting a real part of the impedance measurement at a maximum frequency from a real part of the impedance measurement at a minimum frequency.

3. The method as claimed in claim 1, wherein the polymer resistance is the magnitude of a real part of the semicircle in a Nyquist diagram.

4. The method as claimed in claim 1, wherein the polymer material for vulcanization is any one selected from the group consisting of natural rubber, isoprene rubber, butadiene rubber, styrene butadiene rubber, butyl rubber, ethylene propylene rubber, chlorosulfonated polyethylene, nitrile rubber, acryl rubber, urethane rubber, silicon rubber and fluorine rubber.

5. The method as claimed in claim 4, wherein the measurement of impedance in the wide frequency range employs an impedance spectrum measurement method using the Fourier transform of multiple sinusoidal waves.

6. The method as claimed in claim 4, wherein the measurement of impedance in the wide frequency range employs an impedance spectrum measurement using the transient response Laplace transform.

7. A method for controlling an optimal degree of vulcanization for a vulcanized sample in real time and determining an optimal content of each constituent ingredient of a polymer composition for vulcanization, the method comprising:
   (a) measuring an impedance during a vulcanization process in real time in a frequency range of 1 Hz to 10 kHz so as to evaluate a crosslink degree of the vulcanized sample or the properties of the sample completely vulcanized;
   (b) approximating the measured impedance spectrum to an equivalent circuit model of the sample and determining parameters for resistance and capacitance components of the equivalent circuit model;

(c) determining a polymer resistance Rp from the determined parameters;

(d) determining, as an optimal end point of vulcanization, a time point at which the increasing rate of the polymer resistance Rp rapidly slows down; and (e) determining the optimal content of each constituent ingredient of the composition for vulcanization when the polymer resistance Rp of the sample completely vulcanized is at its minimum.

8. The method as claimed in claim 7, wherein the polymer material for vulcanization is any one selected from the group consisting of natural rubber, isoprene rubber, butadiene rubber, styrene butadiene rubber, butyl rubber, ethylene propylene rubber, chloroprene rubber, chlorosulfonated polyethylene, nitrile rubber, acryl rubber, urethane rubber, silicon rubber and fluorine rubber.

9. The method as claimed in claim 7, wherein the crosslink of the vulcanized sample is any one selected from the group consisting of sulfur crosslink, hybrid crosslink, resin crosslink and peroxide crosslink.

10. The method as claimed in claim 7, wherein the measurement of impedance in the wide frequency range employs an impedance spectrum measurement method using the Fourier transform of multiple sinusoidal waves.

11. The method as claimed in claim 7, wherein the measurement of impedance in the wide frequency range employs an impedance spectrum measurement using the transient response Laplace transform.

12. The method as claimed in claim 7, wherein the equivalent circuit model is an nRC element model, wherein n is a positive integer.

13. The method as claimed in claim 7, wherein the polymer resistance is obtained by subtracting a real part of the impedance measurement at a maximum frequency from a real part of the impedance measurement at a minimum frequency.

14. The method as claimed in claim 7, wherein the polymer resistance is the magnitude of a real part of the semicircle in a Nyquist diagram.

15. The method as claimed in claim 7, wherein the impedance measurement of the vulcanized sample is done with a sample piece positioned between two electrodes.

16. The method as claimed in claim 15, wherein the two electrodes are made from any one metal selected from the group consisting of aluminum, copper, nickel, platinum and stainless steel.

* * * * *